United States Patent [19]

Ferrante et al.

[11] Patent Number: 5,569,259
[45] Date of Patent: Oct. 29, 1996

[54] MODULAR SHAPING AND TRIAL REDUCTION GUIDE FOR IMPLANTATION OF FEMORAL PROSTHESIS AND METHOD OF USING SAME

[75] Inventors: Joseph M. Ferrante; James E. Van Hoeck; Bradley J. Coates, all of Cordova, Tenn.; Leo A. Whiteside, Chesterfield, Mo.

[73] Assignee: Wright Medical Technology, Inc., Arlington, Tenn.

[21] Appl. No.: 380,363

[22] Filed: Jan. 30, 1995

Related U.S. Application Data

[63] Continuation of Ser. No. 975,247, Nov. 12, 1992, Pat. No. 5,415,662, which is a continuation of Ser. No. 839,425, Feb. 20, 1992, Pat. No. 5,176,684.

[51] Int. Cl.⁶ ......................................................... A61F 5/00
[52] U.S. Cl. .............................................. 606/87; 606/86
[58] Field of Search .................................. 606/79, 80, 86, 606/87, 88, 96, 97, 98

[56] References Cited

U.S. PATENT DOCUMENTS

| | | | |
|---|---|---|---|
| 4,474,177 | 10/1984 | Whiteside | 606/88 |
| 4,721,104 | 1/1988 | Kaufman | 606/88 |
| 4,722,330 | 2/1988 | Russell | 606/88 |
| 4,787,383 | 11/1988 | Kenna | 606/88 |
| 4,825,857 | 5/1989 | Kenna | 606/88 |
| 5,035,700 | 7/1991 | Kenna | 606/87 |
| 5,037,423 | 8/1991 | Kenna | 606/86 |

*Primary Examiner*—Sam Rimell
*Attorney, Agent, or Firm*—Walker, McKenzie & Walker, P.C.

[57] ABSTRACT

According to the invention, there is provided a trial implant and method of using same. The implant includes a modular bracket defining a structure having an internal surface adapted to be seated on the distal aspect of a resected femur bone and an external surface with a shape resembling the normal distal condyle of the femur. The bracket has an opening appointed to expose a portion of the resected bone of the femur, including guide structure for guiding a tool along a predetermined path for controlled shaping of a patellar groove in the bone exposed through the opening. Removal of any portion of the bracket or guide structure is unnecessary following the shaping steps prior to performing a trial reduction.

8 Claims, 8 Drawing Sheets

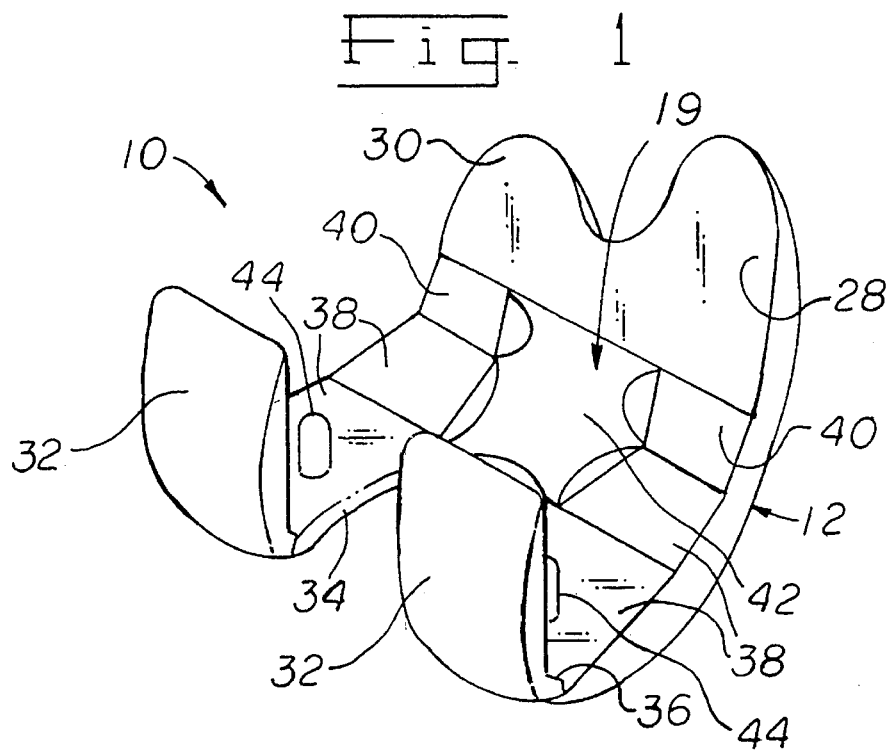
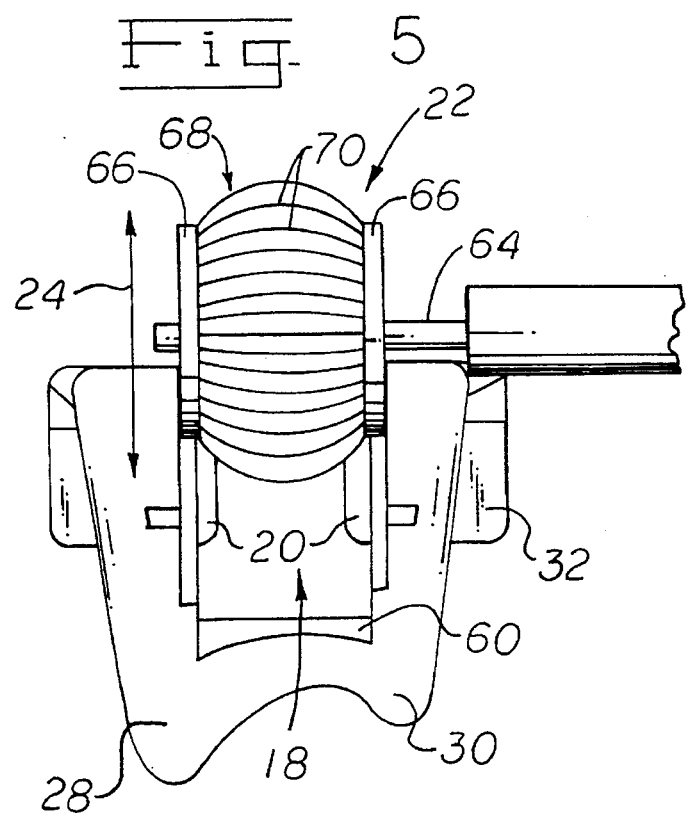

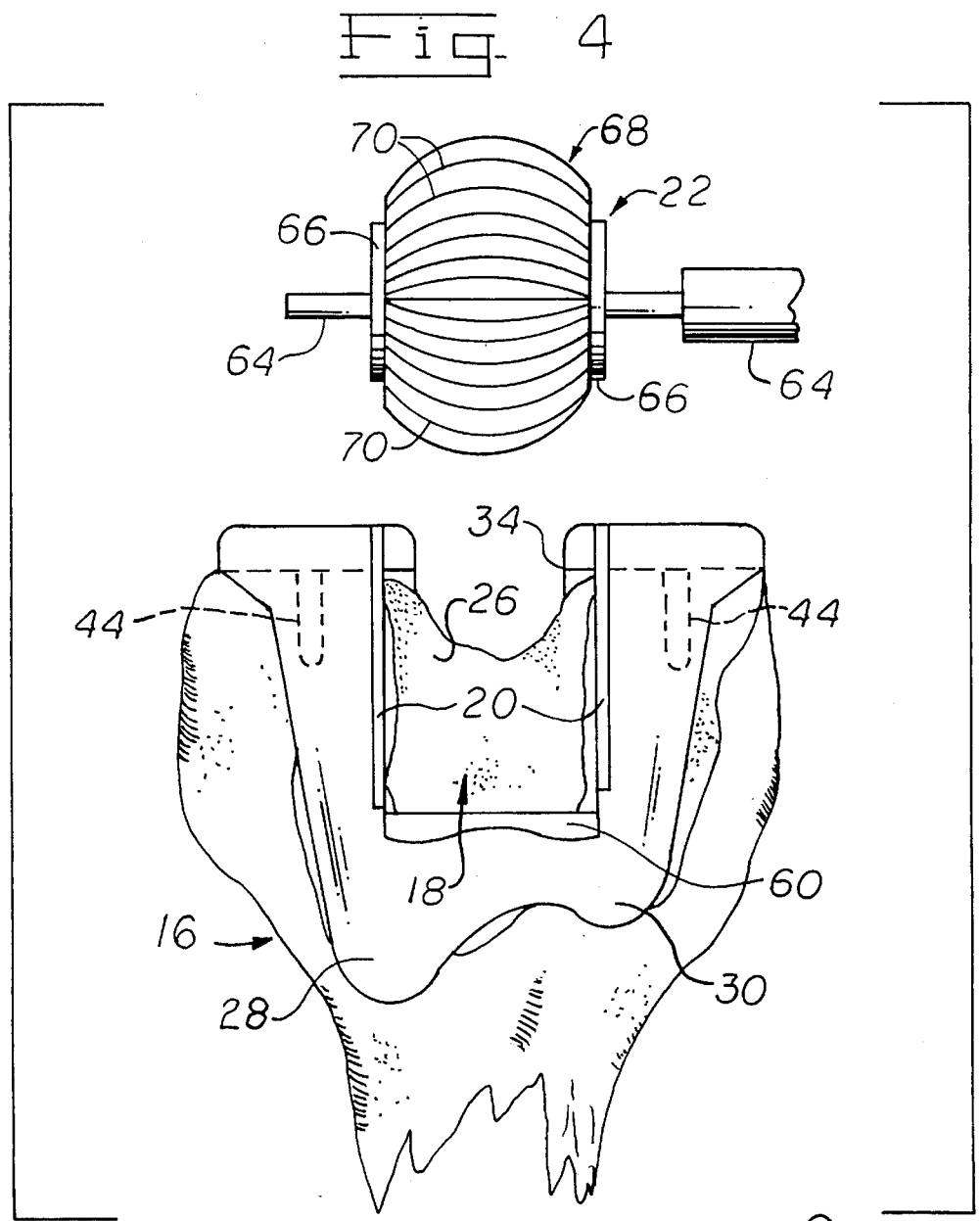

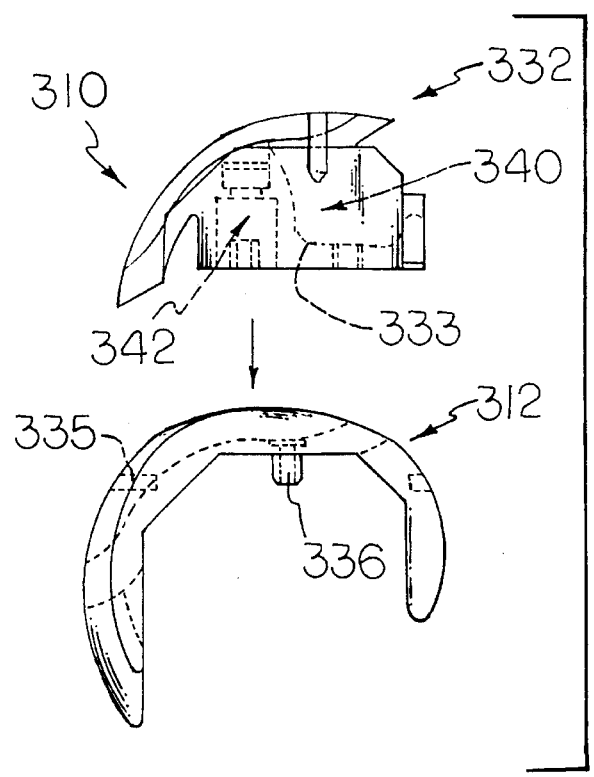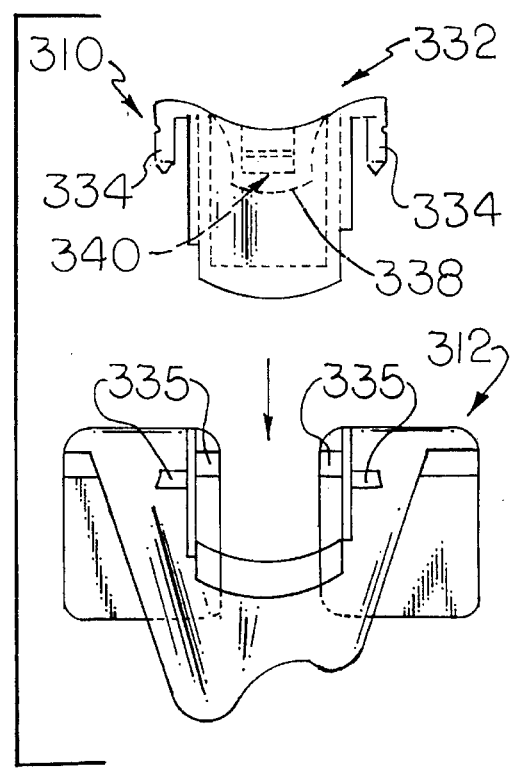
Fig. 10
Fig. 11

MODULAR SHAPING AND TRIAL REDUCTION GUIDE FOR IMPLANTATION OF FEMORAL PROSTHESIS AND METHOD OF USING SAME

CROSS REFERENCE TO RELATED APPLICATIONS

This is a continuation of application Ser. No. 07/975,247 filed on Nov. 12, 1992, entitled "MODULAR SHAPING AND TRIAL REDUCTION GUIDE FOR IMPLANTATION OF FEMORAL PROSTHESIS AND METHOD OF USING SAME," now U.S. Pat. No. 5,415,662, which is a continuation of application Ser. No. 07/839,425 filed on Feb. 20, 1992, now U.S. Pat. No. 5,176,684, entitled "MODULAR SHAPING AND TRAIL REDUCTION GUIDE FOR IMPLANTATION OF POSTERIOR-STABILIZED FEMORAL PROSTHESIS AND METHOD OF USING SAME."

TECHNICAL FIELD

This invention generally concerns orthopedic surgical devices, particularly instrumentation used in preparing a distal femoral bone surface to receive a posterior-stabilized condylar prosthesis, as well as a method of using such instrumentation.

BACKGROUND OF THE INVENTION

During surgical implantation of femoral condylar prostheses, it is typically necessary to utilize some type of tool to gauge whether or not the distal aspect of the femur has been properly sized to receive the condylar implant. This gauge typically resembles the actual prosthesis which will be implanted. The surgeon first "resects" the surface of the bone to match the geometry of the implant by making several cuts as shown, for example, in U.S. Pat. No. 4,474,177 to Whiteside, the entire disclosure of which is expressly incorporated by reference herein and relied upon.

Once the distal aspect of the femur has been resected, a convex patellar groove is formed in the anterior surface of the resected bone, in order to accommodate the mating concave patellar track of the condylar implant. In a total knee replacement, the external distal surface of the condylar implant, including that of the patellar track, articulates with the proximal aspect of an implanted tibial component. A previously devised cutting guide for shaping the patellar groove is the subject of allowed U.S. patent application Ser. No. 462,268, filed Jan. 9, 1990 and assigned to the instant assignee, the entire disclosure of which is expressly incorporated by reference herein and relied upon. Depending upon the degree of knee reconstruction indicated, a patellar prosthesis may also be implanted as shown, for example, in U.S. patent application Ser. No. 466,093, filed Jan. 12, 1990 and also assigned to the present assignee, the entire disclosure of which is expressly incorporated by reference herein and relied upon.

A challenge confronted by condylar implant systems is the need to both accurately form a patellar groove in the resected surface of the distal femur and perform a trial reduction of the knee joint to ascertain proper sizing of the condylar implant. This is conventionally a sequential procedure employing first a guide seated on the resected bone for engaging a shaping tool which forms the patellar groove in the bone. Secondly, a trial condylar implant is seated on the resected surface of the distal femur, having a size and shape resembling that of the permanent condylar prosthesis actually being implanted, after which the trial reduction of the knee is performed by articulating the femur and tibia. Following satisfactory trial reduction, the trial implant is removed and replaced by the permanent condylar implant. A disadvantage of the procedure set forth above is degradation of the bone caused by alternate insertion and removal of separate track cutting and trial implant guides, respectively. Moreover, use of separate track cutting and trial implant guides is relatively inefficient and time-consuming, further complicating the surgical procedure for reconstructing the knee joint.

U.S. Pat. No. 4,721,104 to Kaufman and Whiteside, describes a femoral shaping apparatus employing a template having a straight slot therein for cutting a relatively deep recess for an intercondylar stabilizing housing of a knee implant. The patented system also describes a trial implant module, however, it does not disclose a cutting guide having a curved track useful for forming a groove to accommodate patellar track on such a prosthesis Allowed U.S. patent application Ser. No. 666,153, filed Mar. 3, 1991 and assigned to the instant assignee, shows using common surgical instrumentation to form both a groove and deep recess in the resected distal femur, respectively accommodating a patellar track and intercondylar stabilizing housing of the implant, but does not disclose a modular system also capable of performing a trial joint reduction.

U.S. patent application Ser. No. 666,160, filed Mar. 7, 1991 and also assigned to the instant assignee, shows a device and method which combine the features of a femoral trial implant and patellar track cutting guide, so that the patellar groove may be shaped and a surgical trial reduction of the total knee joint accurately performed Using common instrumentation. However, this patent does not show how such modular instruments could be modified to also form a deep recess in the distal femur to accomodate the intercondylar housing of a posterior-stabilized femoral component.

Accordingly, there remains a need for modular instrumentation which can be employed to form both a patellar groove and deep recess in the resected surface of a distal femur using a common guide which also functions to perform a trial reduction of the total knee joint.

SUMMARY OF THE INVENTION

According to the invention, there is provided a trial implant comprising a modular bracket defining a structure having an internal surface adapted to be seated on the distal aspect of a resected femur and an external surface with a shape resembling the normal distal condyle of the femur. The bracket has an elongated central opening appointed to expose the resected surface of the femur, including means for guiding a first tool along a predetermined path for controlled shaping of a patellar groove in the surface exposed through the opening. Means are provided for guiding a second tool for forming a deep recess in the distal femur to accomodate an intercondylar housing of a posterior-stabilized femoral component and is replaced with an insert covering the opening and provided with a posterior-stabilizing housing which articulates with a proximal aspect of the tibia for interoperative trial reduction of the knee joint without removal of the bracket from the resected distal surface.

According to the invention, a method of implanting a posterior-stabilized femoral prosthesis comprises the steps of resecting the distal aspect of the bone to receive a trial implant thereon. The trial implant provided comprises a bracket defining a modular structure having an internal surface adapted to be seated on the distal aspect of the femur and an external surface formed with a shape resembling the normal distal condyle, including an elongated central opening appointed to expose an anterior distal resected surface of the femur to a first shaping tool. The method further comprises the step of providing means for guiding the first tool along a predetermined path for controlled shaping of the anterior distal surface exposed through the opening. The first tool is moved along the path, cutting or abrading a patellar groove in the distal surface. Means are provided for guiding a second shaping tool during a step which forms a deep recess in the distal surface to accomodate an intercondylar housing of the posterior-stabilized femoral component. An trial insert having a posterior-stabilizing housing and cooperable with the guide means is brought into secure engagement with the opening, covering the area of the patellar groove. The insert and bracket function as a trial implant as the femoral and tibial component are articulated during a step which includes the trial reduction of the total knee joint.

An advantage of this invention is a device and method of using the device by which a patellar groove and deep recess of a posterior-stabilized femoral component may be shaped in a resected femur using common instrumentation which also functions as a trial implant during trial reduction of the total knee joint.

Another advantage of this invention is a method and a device by which excessive wear on the distal aspect of the femur is avoided by replacing the use of multiple instruments With a single modular device.

BRIEF DESCRIPTION OF THE DRAWINGS

The above and other Objects and advantages of the present invention will become apparent to those skilled in the art upon an examination of the following Detailed Description and Drawings which are illustrative of the present invention wherein:

FIG. 1 is a internal perspective view of an existing trial, shown with the first insert in place for a regular condylar implant;

FIG. 2 is a side elevation view of the trial implant of FIG. 1;

FIG. 4 is a frontal view of the modular bracket of the invention seated on the resected distal femur, shown being used in combination with the first cutting tool for shaping the patellar groove in the bone;

FIG. 5 is a frontal external view of the bracket alone, illustrating cooperation of the guide means for the first tool along with that tool;

FIG. 10 is an exploded side elevational view of the bracket of FIG. 8, in combination with a trial insert adapted for reduction in a posterior-stabilized total knee joint;

FIG. 11 is an exploded frontal view of the combination of FIG. 10; and

DETAILED DESCRIPTION OF ONE OR MORE PREFERRED EMBODIMENTS

Figure 3:
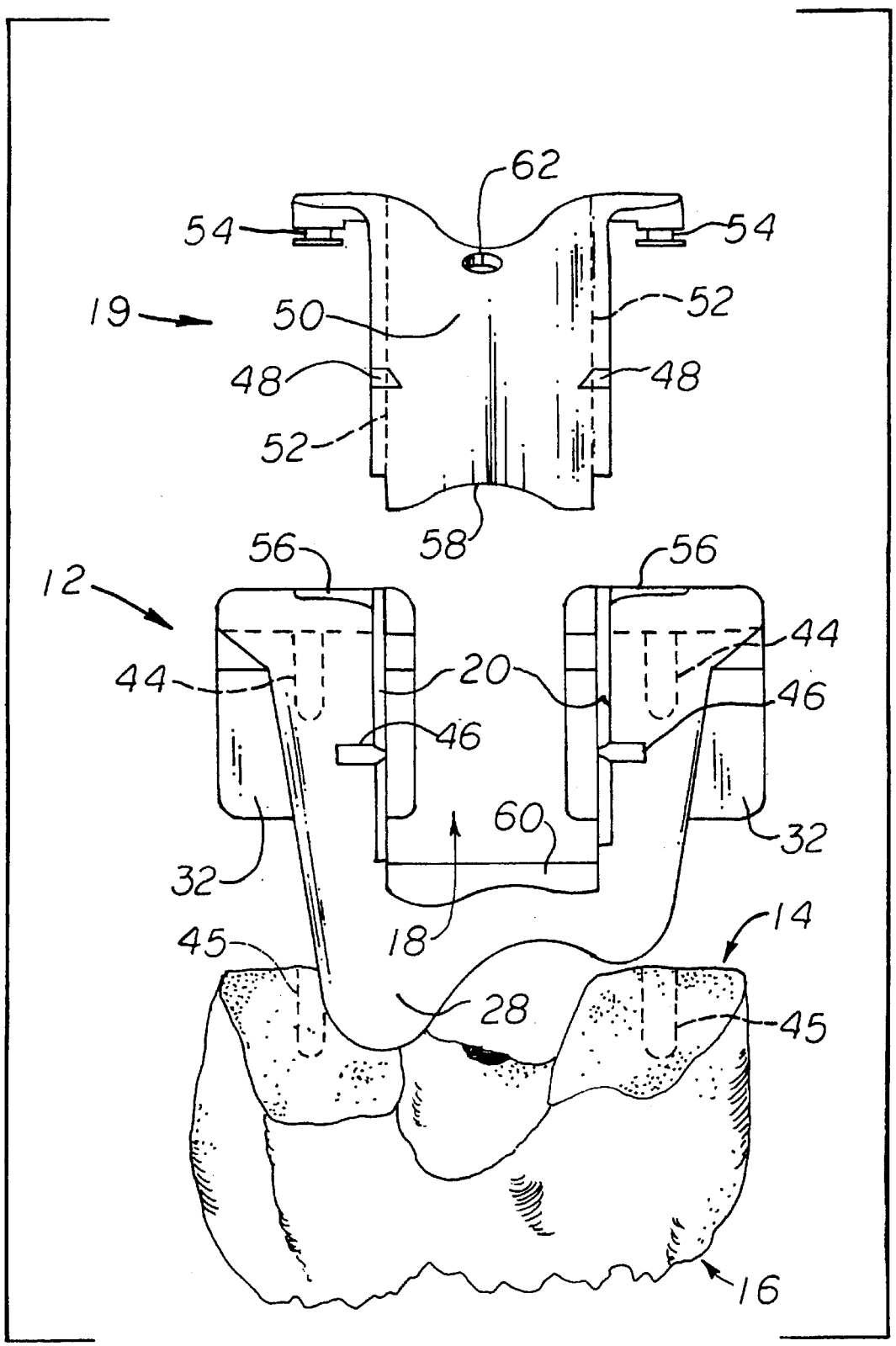
FIG. 3 is an exploded perspective view of the trial implant of FIG. 1, showing the modular bracket being seated on the resected distal femur with the first insert removed.
Figure 6:
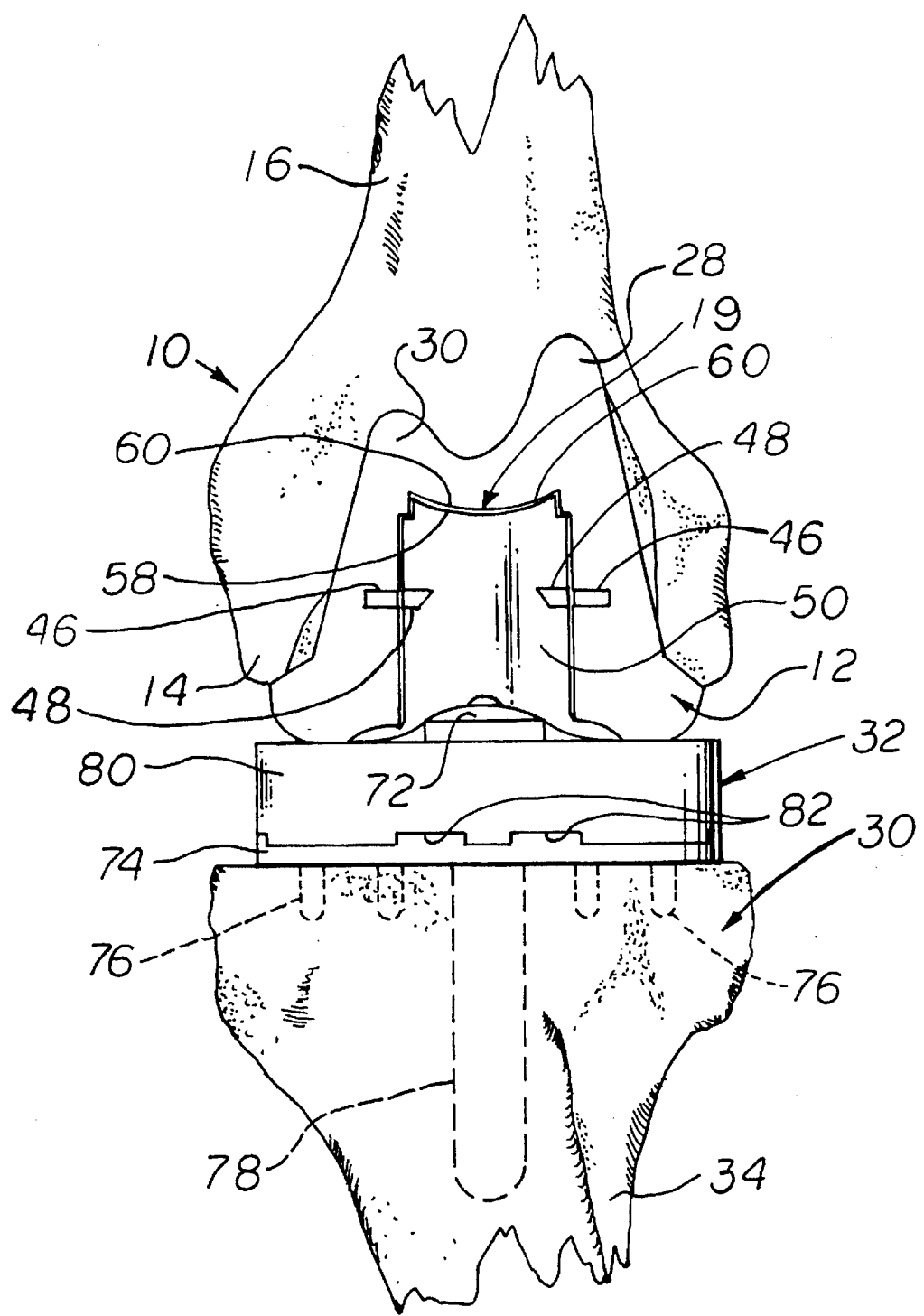
FIG. 6 is an external frontal view of the trial implant of FIG. 1, showing the first insert securely positioned within the opening of the bracket and articulating with a tibial prosthesis during the trial reduction of a non posterior-stabilized knee joint.

A trial implant is generally shown at 10 in FIGS. 1 and 6, comprising a modular bracket, generally indicated at 12, defining a structure having an internal surface (facing the viewer) adapted to be seated on a distal aspect, generally indicated at 14 in FIGS. 3 and 6, of a resected femur bone, shown at 16 in FIGS. 3, 4 and 6. With particular reference to FIGS. 3, 5 and 4, the bracket has an external surface (facing the viewer) resembling the normal distal condyle of the femur and any elongated central opening, generally indicated at 18 which is appointed to expose the resected distal aspect 14 of the femur 16. Means are provided in the form of parallel tracks or channels 20 for guiding a tool, generally indicated at 22 along a predetermined path in the direction of arrow 24 for controlled shaping of a patellar groove 26 (FIG. 4) in the bone exposed through the opening 18. A replaceable insert, generally indicated at 19 (FIGS. 1 and 3), covers the opening 16 and articulates with either the normal surface or a prosthesis 32 which is implanted on the resected surface of the proximal aspect 30 of the tibia 34 during interoperative trial reduction of the knee joint as shown in FIG. 6.

Referring to the FIG. 1, the internal surface of the trial implant 10 is shown comprising a medial 28 and lateral 30 portions of an anterior condylar flange, a pair of posterior condylar flanges 32 which define an intercondylar notch 34 and a series of planar areas. Specifically, the planar areas comprise a smooth metal finish, since tissue ingrowth into the internal surface of the trial implant 10 is not necessary and, in fact, a non-abrasive action is desirable in seating the trial implant 10 on the resected distal aspect 14 of the femur 16. With additional reference to FIG. 2, the planar surfaces which comprise the internal surface of the trial implant, as shown with the insert 19 positioned in =the opening 18 (FIGS. 1–6) include a posterior 36, distal 38 and anterior 40 surface. A humped distal internal contact surface 42 of the trial implant 10, constitutes the internal surface of the insert 19. Likewise, the internal surfaces of the posterior condyles 32 and the medial 28 and lateral 30 portions of the anterior condyle, respectively, also have a smooth metal finish to facilitate onto and off from the resected bone. The cleaner surfaces correspond to the resection cuts made in the distal aspect 14 of the femur 16. A pair of pegs 44 are formed in the planar surface 38 and project into corresponding holes 45, shown in phantom in FIGS. 3 through 4, bored in the distal aspect 14 of the femur 16. It will be appreciated that, in most cases, boring holes into the resected distal femoral surface is unnecessary for accommodating the pegs 44. Instead, after the femur is resected and planed, the area which receives the pegs 44 is made of soft bone, and the pegs are simply pressed into the bone.

Referring to FIG. 3, the bracket 12 has a pair of alignment notches 46 on opposed sides of opening 18, which align with a pair of corresponding notches 48 formed on opposed sides of the insert 19. The insert 19 further comprises a central concave patellar track 50 and a pair of opposed lateral flanges 52 on either side of the patellar track 50. The lateral flanges 52 engage the channels 20 of the bracket 12. The insert is securely positioned in place on the bracket by a pair of opposed studs 54 which meet with a corresponding pair of apertures 56 formed in the external distal surface of the bracket 12. The insert 19 has an interior shoulder 58 which engages in abutment ledge 60 formed in the interior condyle of the bracket 12. The insert 19 may be readily positioned within the opening 18 of the bracket 12 by means of a gripping aperature 62 formed in the patellar track 50 of the insert 19; likewise, the alignment notches 48 may also facilitate interoperative removal and replacement of the insert within the opening 18 as needed.

Referring to FIG. 4, the shaping tool 22 further comprises a drive shaft 64 rotatably mounted by means of a bearing sleeve 66 to a cutting element, generally indicated at 68, having a plurality of convex-shaped ribs 70 which cut and/or abrade the resected surface of the resected surface of the distal femur to form the patellar groove 26.

Referring to FIG. 5, the bearing sleeve 66 extends outwardly from either side of the cutting element 68 and does not rotate with the cutting element 68. Rather, the bearing sleeve 66 rotates independently of the cutting element 68, engaging and traveling along the channels 20 which establishes the predetermined path indicated by the arrow 24 two shapes of patellar groove.

Once the patellar groove 26 has been formed in the manner described above, the insert is replaced into the opening 18 and the knee joint is relocated, as shown in FIG. 63 where the proximal aspect 30 of the tibia 34 has also been resected and a prosthesis 32 implanted, so that the articulating process of the tibial implant engages the patellar track 50 of the condylar prosthesis. The tibial prosthesis 32 may be selected from any of a variety of conventional types available to those skilled in the art. The tibial prosthesis 32 preferably comprises a metal base plate 74 which is implanted into the resected proximal aspect 30 of the tibia 34 by means of pairs of lateral pegs, shown in phantom at 76 and a central long stem 78 which is fit into the intermedullary canal of the tibia 34. The tibial implant 32 is of modular construction, further comprising an upper articulating portion 80, preferably formed of a hard plastic material, for example, high molecular weight polyethylene, to provide a non-degrading articulating surface. The upper portion 80 locks into place within the base 75 by means of an arrangement of notches 82 and the upper portion may be replaced when worn without removing the metal base portion 74 implanted into the bone.

Modular surgical instrumentation and a method of using same as described in conjunction with FIGS. 1–6 above is adapted to form a deep recess in the distal femur to accomodate an intercondylar housing of a posterior-stabilized femoral component, according to the invention, as further shown in FIGS. 7–12. This instrumentation (bracketed in FIG. 7) comprises a bracket 312, which has essentially the same construction as the bracket 12 illustrated in FIG. 1 and 3–4 and need not be further described in detail here. The bracket 312 defines a generally U-shaped structure which is seated on the distal aspect of the resected femur 13 and has the elongated central opening 323 appointed to expose a selected area of the femur, including curved ledges 340, 342 for guiding the first tool, generally indicated at 22 (see FIG. 5), along a predetermined path for controlled shaping of a curved patellar groove in a portion of the selected area exposed through the opening, substantially as described above with reference to FIG. 3. Means generally shown at 300 for guiding a second shaping tool defines a linear bore 302 (shown in phantom) receiving a second tool in the preferred form of an end mill, generally indicated at 304 rotating in the direction of arrow 306, and movable axially in the direction shown by arrow 308, i.e., downwardly toward the resected femur 13 essentially parallel to the long axis of the femoral medullary canal 311 (shown in phantom). Bore 302 may have a pair of slots (not shown) which extend tangentially from the bore for receiving a U-shaped punch of the type shown in aforementioned U.S. Ser. No. 666,153, or an osteotome (not shown), downwardly in the direction of arrow 308 through the bore 302, to form, together with the end mill 304, a relatively deep elongated recess in the femur, as will be described in conjunction with FIG. 11. The guide means 300 further comprises a top 314 which is essentially perpendicular to the long axis of the femur and through which bore 302 is formed.

Referring to FIGS. 7 and 10–12, extending perpendicularly from the top plate 314 are a pair of legs 316 each having seats 318 which extend in an anterior-posterior direction and have a curved shape to engage the ledges 340, 342 of bracket 312. Guide means 300 is aligned with respect to bracket 312 by a pair of positioning holes 320 which respectively engage a pair of pegs 324 projecting distally from the guide means 300, to securely lock the guide means 300 into proper position with respect to bracket 312. The bracket 312 can be further secured either to the bone, guide means or both by any suitable arrangement of clips, clamps or the like as will be readily appreciated by those skilled.

Figure 7:
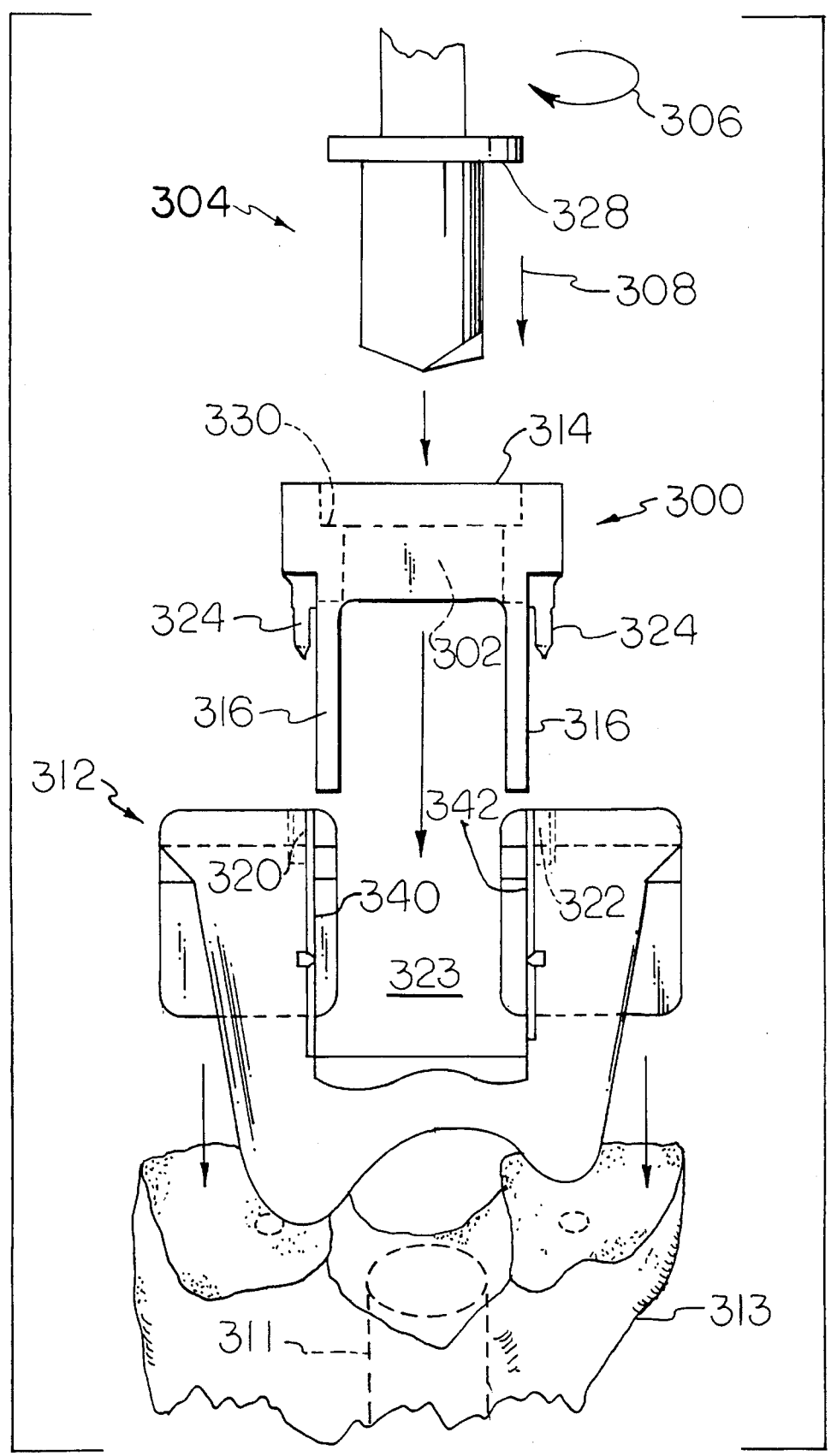
FIG. 7 is an exploded frontal view of the assembly for forming a deep recess in the distal femur to accomodate an intercondylar housing for a posterior-stabilized femoral component.
Figure 8:
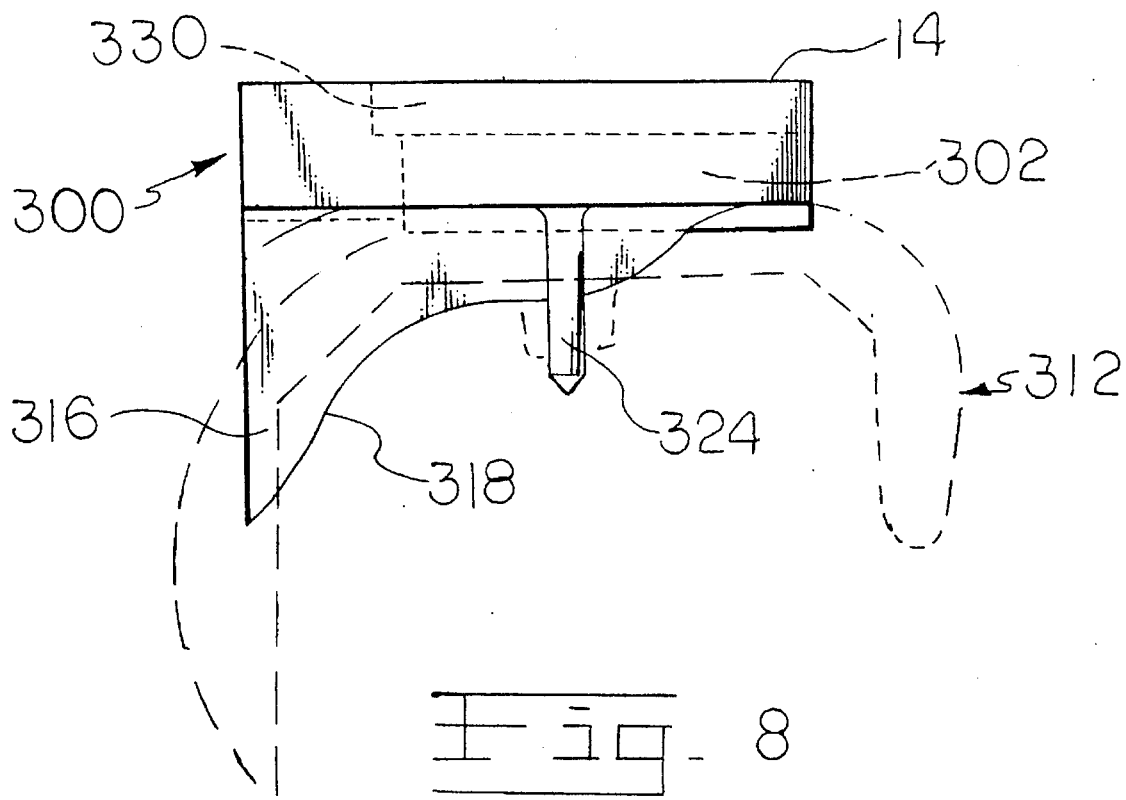
FIG. 8 is a side elevational view of the means for guiding the second tool of the invention for forming a deep recess in the distal femur, shown resting on the bracket which is indicated in phantom.
Figure 9:
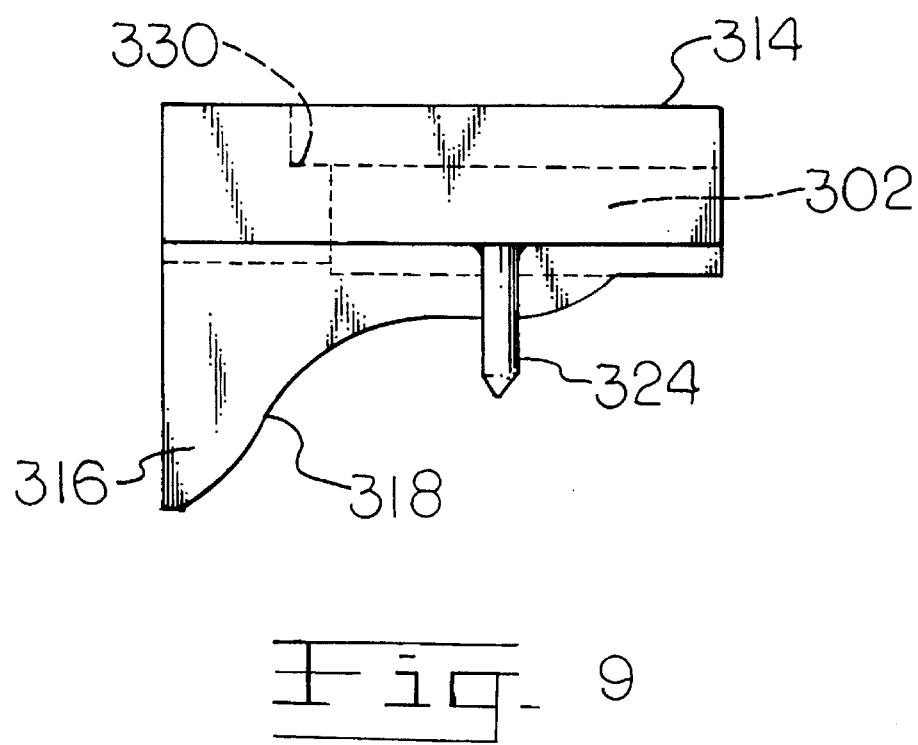
FIG. 9 shows the guide means of FIG. 8 alone apart from the bracket.

End mill 304, shown in FIGS. 7–9, has a shoulder 328 which bottoms-out in the stop 330 formed at the distal end of bore 302. After end mill 304 is thus brought down into the surface of the resected femur 13 and then withdrawn, the punch or osteotome alluded to above is impacted with a mallet or the like to finish forming an elongated deep recess for the intercondylar stabilizing housing, until the tip of such punch or osteotome reaches the bottom of the hole formed by end mill 304.

Figure 12:
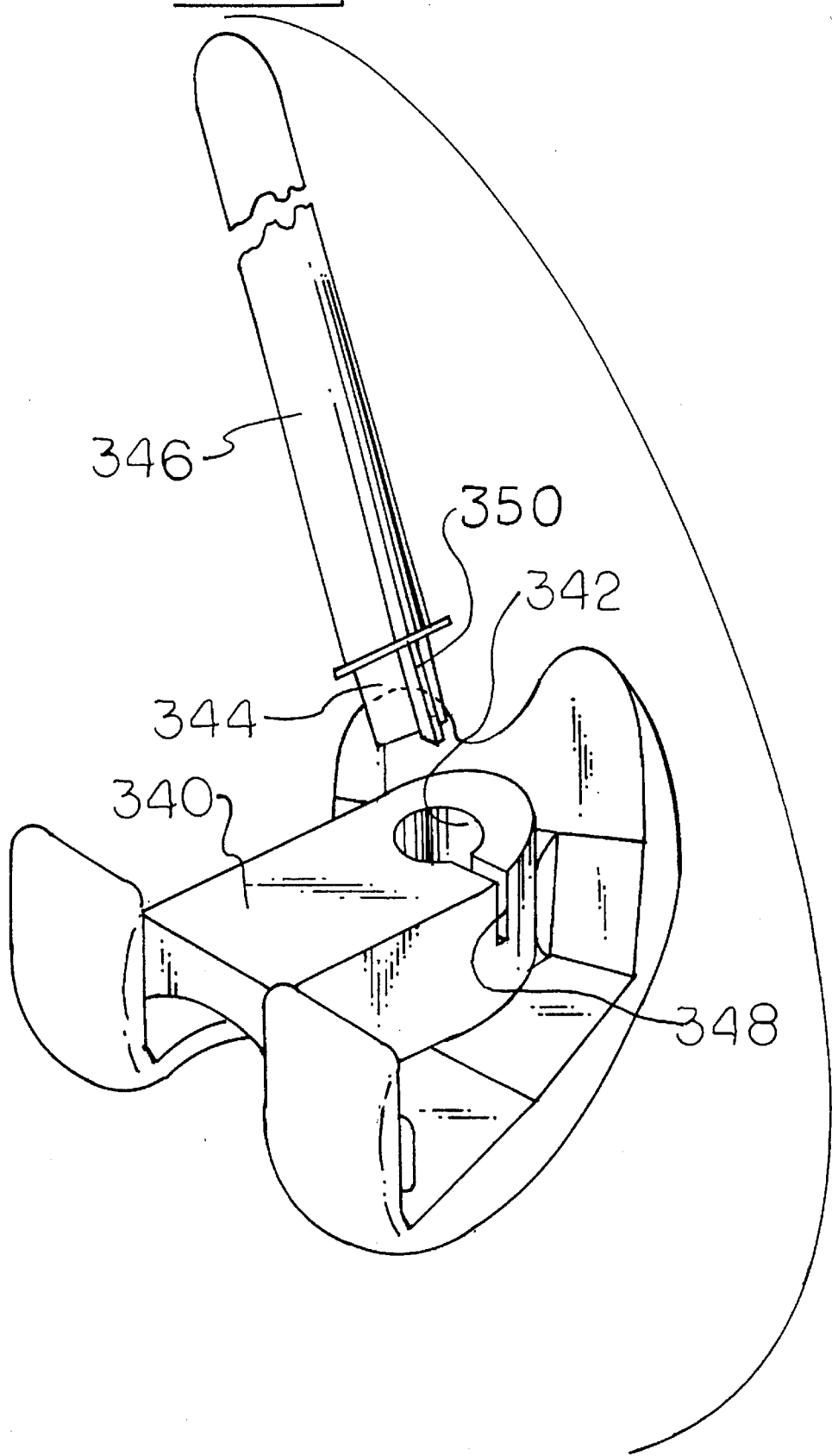
FIG. 12 is an external perspective view of a femoral trial component having a posterior-stabilizing housing with modular revision stem.

Referring to FIGS. 10–11, following formation of the deep recess, the surgeon replaces the end mill guide 300 with a different insert, generally shown at 332 which has been modified with a posterior-stabilizing housing, the combination of insert and bracket being collectively denoted by reference numeral 310. The insert 332 is positioned on the bracket 312 by locator fingers 334 engaging slots 335, the bracket being, in turn, located on the bone using pegs 336 (FIG. 10). The modified insert 332 further comprises an internal wall, indicated in phantom at 338, defining the housing 340, also shown in phantom in FIGS. 10–11. A tapered female morse-type connector 342 is provided adjacent the housing 340, receiving a male morse-type connector 344 from a trial stem 346 via keyway 348 which receives key 350, as shown by FIG. 12. Except for the housing 340 and tapered connectors 342, 344, the structure and function of the modular trial component of FIGS. 10–12 is used in performing trial reduction of the knee joint similarly to the femoral trial component discussed relative to FIGS. 1–6 above.

The method of the invention comprises the steps of seating the bracket described above on the distal aspect of the resected femur and moving the first shaping tool along the curved track to form a patellar groove in a selected area thereof. The first shaping tool is then withdrawn and, leaving the bracket in place, while the end mill guid discussed above relative to FIGS. 7–9 is seated on the curved track so that the slotted bore of the guide is accurately aligned with the opening of the bracket, after which the end mill is introduced through the bore to form a deep recess accommodating the intercondylar-stabilizing housing of the trial implant and the trial reduction of the posterior-stabilized knee joint is performed.

These and other variations of the present invention may be made which fall within the scope of the appended claims even though such variations were not specifically discussed above.

That which is claimed is:

1. A method of implanting a condylar prosthesis onto the proximal aspect of a resected femur comprising the steps of:

(a) resecting the distal aspect of the femur to receive a trial implant thereon;

(b) providing a trial implant including, in combination, a bracket defining a modular structure with an internal surface adapted to be seated on the distal aspect of the femur and an external surface formed with a shape resembling the normal distal condyle, including an opening appointed to expose a selected portion of the anterior distal resected surface of the femur to a shaping tool and guide means joined to the bracket as an integral, one piece unit for guiding the tool along a predetermined path for controlled shaping of a patellar groove in the exposed portion of the femur through the opening;

(c) moving the shaping tool along the guide means, cutting or abrading a patellar groove in the selected portion of the femur exposed through the opening; and (d) performing a trial reduction of the knee joint, while the bracket remains seated on the distal aspect of the femur and without removing any portion of the modular bracket or guide means.

2. A method of implanting a condylar prosthesis onto the proximal aspect of a resected femur comprising the steps of:

(a) resecting the distal aspect of the femur to receive a trial implant thereon;

(b) providing a trial implant including, in combination, a bracket defining a modular structure with an internal surface adapted to be seated on the distal aspect of the femur and an external surface formed with a shape resembling the normal distal condyle, including an opening appointed to expose a selected portion of the anterior distal resected surface of the femur to a shaping tool and guide means joined to the bracket for guiding the tool along a predetermined path for controlled shaping of a patellar groove in the exposed portion of the femur through the opening;

(c) moving the shaping tool along the guide means, cutting or abrading a patellar groove in the selected portion of the femur exposed through the opening;

(d) performing a trial reduction of the knee joint, without removing any portion of the modular bracket or guide means;

(e) providing a means for guiding a second tool to form a deep recess in the distal femur for accommodating a posterior-stabilizing housing of the femoral component;

(f) forming the deep recess with the second tool; and (g) placing a trial insert formed with a posterior-stabilizing housing securely over the opening.

3. A femoral trial implant comprising:

(a) a modular bracket defining a structure having an internal surface adapted to be seated on the distal aspect of a resected femur and an external surface with a shape resembling the normal distal condyle of the femur, including an opening appointed to expose a selected portion of the resected femur;

(b) guide means joined to the bracket for guiding a tool along a predetermined path for controlled shaping of a patellar groove in the exposed portion of the femur through the opening;

the bracket and guide means including no structure that would prevent proper trial reduction of the knee joint so that the external surface of the bracket articulates with a proximal aspect of the tibia for interoperative trial reduction of the knee joint with no portion of the bracket or guide means preventing proper trial reduction of the knee joint and so that proper trial reduction of the knee joint can be performed after the controlled shaping of a patellar groove therein without removing any portion of the bracket or guide means; and (c) means for guiding a second tool for forming a deep recess in the distal femur to accommodate an intercondylar housing of a posterior-stabilized femoral component.

4. A femoral trial implant for a knee joint, the trial implant comprising:

(a) a trial body having an internal surface adapted to be seated on a resected portion of a femur of the knee joint, having an external surface, and having an opening appointed to expose a portion of the femur, the opening having opposed sides; and (b) a trial insert covering the opening in the trial body and having a distal surface adapted to articulate with a portion of the knee joint during interoperative trial reduction of the knee joint without removing any portion of the trial body or trial insert.

5. The trial implant of claim 4 wherein at least a portion of the opposed sides of the opening in the trial body includes a track adapted to guide a tool along a path to form a patellar groove in the portion of the femur exposed through the opening extending along the side of the opening.

6. The trial implant of claim 5 wherein the track includes a channel formed along each of the opposed sides of the opening.

7. A method of shaping and performing a trial reduction of a knee joint comprising the steps of:

(a) seating a trial implant on a resected portion of a femur of the knee joint, the trial implant having an internal surface adapted to be seated on the femur, having an external surface, and having an opening appointed to expose a portion of the femur, the opening having opposed sides;

(b) covering the opening in the trial implant with a trial insert having a distal surface adapted to articulate with a portion of the knee joint during interoperative trial reduction of the knee joint;

(c) performing a trial reduction of the knee joint without removing any portion of the trial implant or trial insert; and (d) moving a forming tool along at least a portion of the opposed sides of the opening of the trial implant to form a patellar groove in the portion of the femur exposed through the opening in the trial implant.

8. The method of claim 7 wherein each opposed side of the opening in the trial body includes a channel formed adapted to guide a tool along a path to form a patellar groove in the selected portion of the distal surface of the femur exposed through the opening extending along the side of the opening; and wherein the step of moving a forming tool along the portion of the opposed sides of the opening in the trial implant includes moving a forming tool along the channel of one side of the opening in the trial implant and along the channel of the other side of the opening in the trial implant.

* * * * *